United States Patent [19]

Simmonds et al.

[11] Patent Number: 4,469,792

[45] Date of Patent: Sep. 4, 1984

[54] BLOOD GAS CALIBRATION AND CONTROL FLUID UTILIZING STROMA-FREE HEMOGLOBIN

[75] Inventors: Richard S. Simmonds, Landing, N.J.; Wells P. Owen, Nyack, N.Y.

[73] Assignee: Allied Corporation, Morris Township, Morris County, N.J.

[21] Appl. No.: 290,174

[22] Filed: Aug. 5, 1981

Related U.S. Application Data

[63] Continuation-in-part of Ser. No. 221,640, Dec. 31, 1980, abandoned, and a continuation-in-part of Ser. No. 221,639, Dec. 31, 1980, abandoned.

[51] Int. Cl.³ .................... C09K 3/00; G01N 33/68; G01N 33/96
[52] U.S. Cl. ........................ 436/11; 436/15; 436/16; 436/17; 424/101; 424/177
[58] Field of Search ............... 424/101, 177; 436/11, 436/15, 16

[56] References Cited

U.S. PATENT DOCUMENTS

| | | |
|---|---|---|
| 3,681,255 | 8/1972 | Wilfore .......................... 436/11 |
| 3,859,049 | 1/1975 | Ware et al. ..................... 436/11 |
| 3,973,913 | 8/1976 | Louderback .................... 436/11 |
| 3,991,181 | 11/1976 | Doczi et al. .................. 424/101 |
| 4,001,142 | 1/1977 | Turner ........................... 436/11 |
| 4,001,401 | 1/1977 | Bonsem et al. ................ 424/101 |
| 4,133,874 | 1/1979 | Miller et al. ................... 436/11 |
| 4,163,734 | 8/1979 | Sorensen et al. ............... 436/11 |
| 4,279,775 | 7/1981 | Louderback et al. ........... 436/11 |
| 4,289,648 | 9/1981 | Hoskins et al. ................. 436/11 |
| 4,299,728 | 11/1981 | Cormier et al. ................ 436/11 |
| 4,343,797 | 8/1982 | Ecanow .......................... 436/15 |
| 4,425,334 | 1/1984 | Hunt ............................. 424/101 |

FOREIGN PATENT DOCUMENTS 2031148  4/1980  United Kingdom ............ 436/11

*Primary Examiner*—Teddy S. Gron
*Attorney, Agent, or Firm*—Webb, Burden, Robinson & Webb

[57] ABSTRACT

A reference fluid for the calibration and control of blood gas instruments is comprised of substantially pure stroma-free hemoglobin solution, a buffering agent, a source of bicarbonate ion and predetermined amounts of gases found in in vivo blood.

12 Claims, No Drawings

BLOOD GAS CALIBRATION AND CONTROL FLUID UTILIZING STROMA-FREE HEMOGLOBIN

CROSS REFERENCE TO RELATED APPLICATIONS

This application is a continuation-in-part of U.S. application Ser. No. 221,640 and U.S. application Ser. No. 221,639, both filed Dec. 31, 1980, both now abandoned.

BACKGROUND OF THE INVENTION

1. Field of the Invention

This invention relates to blood gas calibration and control fluids and, more particularly, fluids containing hemoglobin.

2. Description of the Prior Art

Blood gas tests are frequently used in health care facilities to determine abnormalities in pulmonary function. These parameters commonly used in determining pulmonary abnormalities are blood pH, $P_{CO_2}$ and $P_{O_2}$. The tests are performed by drawing blood from the patient and introducing this blood into specialized equipment which determines the various parameters to be measured. The specialized equipment must be calibrated frequently to determine if the readouts on values for patient blood are accurate. This calibration involves introducing various solutions or gases having predetermined amounts of constituents which are present in in vivo blood.

After the testing equipment has been calibrated it is necessary to assure maintenance of the calibration routine. For this reason the instrument is frequently tested with blood gas controls which quickly and readily determine any unexpected analytical deviations. The blood gas controls do not have absolute values for pH, $P_{CO_2}$ and $P_{O_2}$. Instead ranges are provided; if the instrument responds within the specified range, the accuracy of the calibration is assured.

Typical blood gas control techniques and solutions are taught in U.S. Pat. No. 3,859,049; *Clin. Chem.* 24, p. 793-795, 1978 by Steiner et al.; U.S. Pat. No. 3,973,913; and U.S. Pat. No. 4,001,142.

In calibrating or controlling of the instrumentation for blood gas analysis, it is desirable to use a material containing the predetermined amount of blood constituents which most approximates the function of blood to obtain accurate readings. Thus, the ideal solution would be blood having predetermined amounts of constituents to calibrate the instrumentation. However, use of blood as a calibration or control fluid is impractical because of instability and degradation problems upon aging, and the generation of methemoglobin on aging which destroys the oxygen carrying function of the hemoglobin constituents. Furthermore, with whole blood it is difficult if not impossible to adjust the pH accurately and reproducibly.

Thus, several other types of solutions have been proposed and used as blood gas calibration standards or controls. The most widely used are aqueous solutions such as taught in U.S. Pat. No. 4,001,142. These solutions have several problems associated with their use. Aqueous controls have excellent shelf life. However, once the seal is broken the aqueous control must be used immediately since when the aqueous control solution is open to the environment, there is rapid exchange of the dissolved gases and the control fluid with the external environment thereby changing the concentration of the assayed constituents. Such exchanges result in inaccurate recovery of the assayed parameters.

In addition, a small amount of liquid which has been exposed to, and therefore, equilibrated with the atmosphere, or other *gas* is present in the instrument sample chamber. The gas permeable membranes separating the electrode from the chamber also may contain trapped gas. This residue can mix with the sample and cause changes in the gaseous constituents, especially oxygen. With whole blood these changes are effectively negated, due to the reversible interaction of hemoglobin and oxygen which provides a high "oxygen buffer capacity". Typical aqueous blood gas controls contain no such "oxygen buffer capacity" and are, therefore, easily contaminated during sample handling and within the sample chamber.

The values obtained for the assayed constituents in whole blood (pH, $P_{CO_2}$ and $P_{O_2}$) are dramatically affected by the temperature of the sample chamber in which the sample is being analyzed. The control material must, therefore, respond to temperature changes in the instrument similar to whole blood. No typical aqueous blood gas control responds appropriately to temperature induced value changes in all measured parameters. The control material of the present invention containing stroma-free hemoglobin closely simulates the response of whole blood with respect to all measured parameters.

To avoid some of these problems treated red cells in a buffer have been used as a blood gas control. Louderback U.S. Pat. No. 3,973,913 teaches such a blood control standard in which the cells are treated with aldehyde to render the cell membrane less sensitive to lysing and inhibit the metabolism of the cell. The stability of the control when opened is improved but the shelf life is significantly decreased. However, the treatment effects the hemoglobin so that it is apparently no longer physiological. In order to provide an effective oxygen buffer system, the hemoglobin contained in the control must be in such a form that its oxygen affinity is similar to that of whole blood. The controls containing treated erythrocytes contain hemoglobin that has an enhanced oxygen affinity and, therefore, suffer from a reduced oxygen buffer capacity.

A quality control material for blood gas analysis must also be convenient to use and thus minimize pre-analytical variables. If it is extremely difficult to prepare the ampulized sample for analysis, then the potential for error increases. Controls containing treated red cells must be carefully re-equilibrated at 37° C. In addition, the treated red cell controls may only be kept re-equilibrated for 30 minutes before discarding.

Thus, it is desirable to use a calibration solution which functions as nearly as possible to blood while eliminating the problems associated with the use of blood as a blood gas control or calibration fluid. In accordance with the present invention, a blood gas control fluid is provided which approximates the function and the gas carrying ability of human blood without the stability problems associated with blood. Like whole blood, the blood gas reference fluid of the present invention incorporates hemoglobin as a reversible oxygen buffer system thus minimizing any errors due to contamination during handling and analysis. The stroma-free hemoglobin has near normal oxygen affinity. The control fluid re-equilibrates at normal room temperature and may be re-equilibrated for up to 48 hours before assay without deleterious effects.

A further advantage of the present invention is the deep red color of the hemoglobin which allows easy visualization within the sample chamber of the analyzer. Like whole blood, this property readily shows the presence of any trapped air bubbles accidently introduced into the measuring chamber.

BRIEF DESCRIPTION OF THE INVENTION

A reference fluid for the calibration and control of blood gas instruments is comprised of substantially pure stroma-free hemoglobin solution, a source of bicarbonate ion, a buffering agent and predetermined amounts of gases present in in vivo blood and specifically oxygen and carbon dioxide.

The stroma-free hemoglobin provides an effective oxygen buffer system. Its oxygen affinity is nearly the same as whole blood and, in fact, simulates the response of whole blood with respect to all measured parameters.

A source of bicarbonate ion is necessary to control the $CO_2$ content and may be used as a buffer to adjust the pH of the reference fluid. Sodium carbonate is an excellent source of bicarbonate ion and may be present in amounts up to 75 millimoles/liter of solution. A phosphate buffer such as $Na_2HPO_4$ is also desirable. An electrolyte source such as sodium chloride, potassium chloride, calcium chloride, etc. may be added. It should be noted that all the additions are physiological; they are present in normal blood.

A broad spectrum antibiotic such as gentamicin or penicillin may also be added to assist in processing by controlling unwanted microbial growth during the processing.

Finally, predetermined amounts of the gases normally present in in vivo blood, generally $O_2$ and $CO_2$, and an inert gas such as $N_2$ are present. A typical blood gas control is prepared at three levels to simulate the clinically significant acid base respiratory balance and function. The $P_{O_2}$ will range from 10 to 500 mm. Hg at 37° C. The $P_{CO_2}$ will range from 5 to 100 mm. Hg at 37° C. The pH will range from 6.8 to 8.0 at 37° C.

DETAILED DESCRIPTION OF THE INVENTION

The fluid utilized in the blood gas control is an aqueous solution of substantially pure stroma-free hemoglobin. "Substantially pure" as used herein means and refers to the hemoglobin being free of proteins, lipoproteins, enzymes and other blood constituents which tend to degrade the hemoglobin.

The preparation of stroma-free hemoglobin is known in the art. For example, suitable stroma-free hemoglobin may be prepared by the process disclosed in "An Improved Stroma-Free Hemoglobin Solution" by Greenberg et al.; *Surgical Forum* V. 26, pp. 53-55 (1975); "Further Studies with Stroma-Free Hemoglobin Solution" by Rabiner et al.; *Annals of Surgery*, pp. 615-622 (April 1970); "Accute Oxygen Supply by Infusion of Hemoglobin Solutions" by Bonhard; *Federation Proceedings* V. 34, No. 6, pp. 1466-1467 (May 1975); "Blood Substitute and Blood Plasma Expander Comprising Polyhemoglobin" by Bonsen et al., U.S. Pat. No. 4,001,401; and "Characteristics of Stroma-Free Hemoglobin Prepared by Crystallization" by DeVenuto et al.; *J. Lab. Clin. Med., pp.* 509-516 (March 1977). Broadly speaking, washed red cells are lysed, the stroma precipitated and the supernatant containing the stroma-free hemoglobin separated from the precipitate by centrifugation. The stroma-free hemoglobin should be sterile filtered.

A particularly useful method of preparing stroma-free hemoglobin is taught in U.S. patent application Ser. No. 290,175, entitled "Process For The Preparation Of Stroma-Free Hemoglobin Solutions" of Simmonds et al., filed the same day as this application. Said patent application is incorporated herein by reference and made a part hereof.

The substantially pure stroma-free hemoglobin solution is adjusted in order to provide a hemoglobin solution of 1 to 30 percent hemoglobin and preferably about 6 to 18 percent hemoglobin. During the adjustment it is desirable to add nongaseous constituents of the blood gas control. This may be accomplished by direct addition of solid materials, as concentrates or in a diluent solution.

In one method of calculation of diluent required, the following equations are used to determine the quantity of such diluent: ((hemoglobin concentration) (volume of hemoglobin solution))/desired percentage of hemoglobin solution=final volume of hemoglobin solution at the desired percentage; and (volume at desired percentage)−(present volume)=quantity of diluent required.

Diluents can be prepared which include various concentrations of the desired constituents. For example, where $Na_2HPO_4$ (in the form of $Na_2HPO_4 \cdot 12H_2O$), sodium chloride, and an antibiotic such as gentamicin or the like are used, the determination of addition can be calculated as follows: (desired molar concentration) (final volume) (358.1 g/M)=grams $Na_2HPO_4 \cdot 12H_2O$ to be added.

In the case of sodium chloride, the calculation would be: (desired concentration of NaCl) (diluent volume) (58.5 g/M)=required amount of solid NaCl. For gentamicin sulfate the calculation would be: (milligrams antibiotic/liter) (final volume) (1/0.6)=grams of antibiotic required.

In preparing the diluent, the required ingredients are added to the appropriate quantity of sterile deionized water.

$Na_2CO_3$ is then added as a buffer for pH control to the blood gas calibration solution. The experimental determination of the appropriate quantity of $Na_2CO_3$ is done by obtaining small aliquots of the diluted hemoglobin solution to which varying amounts of sodium carbonate are added. The aliquots are then tonometered at 25° C. with the appropriate gas mixture (preferably $O_2$ and $CO_2$). The pH of the tonometered solutions are determined by analysis on a blood gas analyzer and additional aliquots are prepared to achieve the desired pH. Preferably the gas mixtures range from up to 50% $O_2$ and up to 20% $CO_2$. After the pH is tested and it is outside the desired range of pH (the preferable pH is 7.1 to 7.6), additional $Na_2CO_3$ or additional hemoglobin solution may be added to obtain the correct pH. Once the correct amount of $Na_2CO_3$ to be added to the diluent is determined, $Na_2CO_3$ in the proper amount is added with mixing.

After the bulk diluent has been prepared, it is added to the hemoglobin slowly with constant stirring. The hemoglobin solution diluted to the desired level of in vivo blood gas constituents is then sterile filtered and stored between 2° and 8° C. The filtered hemoglobin solution is tested to assure absence of microorganisms. If growth is observed, the hemoglobin solution should be refiltered.

After the sterile hemoglobin solution has been obtained, it is warmed to 10° to 40° C. and equilibrated by use of a gas permeable membrane. A countercurrent of gas which has been warmed to the solution temperature and humidified to saturation is fed into the vessel to maintain an atmosphere over the solution of the same gas with which the solution is equilibrated. Samples are removed from the solution during equilibration and tested on a blood gas analyzer. Sodium carbonate solution may be introduced through a sterilizing filter during the equilibration the achieve the desired pH if necessary. The equilibration solutions will show stable values for pH, $P_{O_1}$ and $P_{CO_2}$. The bulk container for the blood gas reference fluid is purged with the gas used for equilibration. The equilibrated hemoglobin solution is then pumped through a sterile filter apparatus and filled into sterile, gas impermeable ampules or other suitable containers which have been preflushed with the equilibrated gas solution. The container is sealed under an atmosphere of the same gas. The invention will be more fully illustrated by reference to the following examples.

EXAMPLE 1

Outdated human blood cells were charged to a 1 liter centrifuge bottle with an air space allowed thereover. Sterile wash solution consisting of 0.05 moles/liter of $Na_2HPO_4$ and 0.22 moles/liter NaCl is charged at a temperature of 2° to 8° C. to the centrifuge bottles until full. The ratio of wash solution to cells was approximately 1:1. Several such bottles were prepared. The bottles were capped and the wash solution mixed with the blood by inversion. The bottles were placed in a centrifuge and centrifuged at 4,200 rpm (4,700×g) for 10 minutes. The centrifuge and rotor along with the centrifuge bottles were precooled to 5° C. to prevent methemoglobin formation.

After centrifugation, the supernatant wash solution was aspirated from the bottles. The bottles with the packed cells therein were filled with the same wash solution as above described and mixed by shaking and inversion. Centrifugation and aspiration of supernatant was repeated. The bottles with packed cells therein were filled with cold (2° to 8° C.) sterile 0.85 percent NaCl solution, mixed by inversion, centrifuged and aspirated as previously described. The ratio of sodium chloride solution to cells was 350 ml./unit of cells. The washed cells were poured into a funnel covered with layers of coarse and fine nylon mesh, the coarse nylon mesh having a mesh size of 120 microns and the fine nylon mesh having a mesh size of 40 microns. The nylon mesh retained the clumped white cells and other foreign matter which was present. The red cells were collected in a graduated cylinder in order to measure the amount of reagent required for stroma precipitation.

The pooled cells were disrupted by sonication using an ultrasonic probe equipped with a continuous flow cell. Cold water was passed through the jacket of the cell to avoid excess heating causing the formation of methemoglobin. The cells were pumped through the disruption cell at a speed of 300-350 ml./minute for a total of 5 passes. At the end of the 5 passes the residual cell count was less than or equal to 250,000/cu. mm. The cell lysate, forming a mixture of stroma and cytoplasmic components including hemoglobin, was collected and a 20% solution of calcium chloride was added with agitation thereto. The ratio of calcium chloride solution to cells was 50 ml. calcium chloride/liter of cells. After all of the calcium chloride had been added, the hemoglobin-stroma-calcium chloride admixture was mixed for 10 minutes. Five grams of dextran sulfate/liter of cells was added as a powder to the above admixture and mixed for 30 minutes. After 30 minutes, no undissolved material remained. 0.1 moles of $Na_2HPO_4$ (in the form of $Na_2HPO_4.12H_2O$)/liter of cells was added to the mixture and mixed for 30 minutes. Immediately after the addition of the $Na_2HPO_4$ the total admixture was cooled to 2° to 8° C. and allowed to stand overnight (16 hours). The admixture was centrifuged at 4,000 rpm (4,700×g) for 90 minutes. Supernatant hemoglobin solution was collected and the complexed stroma and other lipoprotein constituents remained as the precipitant in the centrifuge bottles.

0.1 mole/liter of solid NaCl was added to the supernatant hemoglobin solution. The solution was passed through a Cuno CPX 90S filter cartridge followed by a Pall AR (0.2 micron). The filtrate was dialyzed by passing it through a series of C-DAK-2.5D artificial kidneys using a countercurrent flow of cold 0.1 molar NaCl solution. Subsequent to dialysis the solution was freed of microbial contamination by passage through a 0.2 micron filter and collected in a sterile bottle. The hemoglobin solution prepared had the following characteristics: 27 percent hemoglobin, 2 percent methemoglobin, and free of microorganisms.

The stroma-free hemoglobin solution having a concentration of 27 percent required 55.6 milliliters of hemoglobin solution to 44.4 milliliters of diluent to provide 100 milliliters as a 15 percent solution of substantially pure stroma-free hemoglobin according to the equations previously set forth. The final blood gas control was to have a pH of 7.4, $P_{O_2}$ of 105 mm. Hg. and $P_{CO_2}$ of 40 mm. Hg. at 37° C. Three aliquots of 44 milliliters each were prepared in accordance with the calculations previously set forth to obtain solutions of 0.05 molar $Na_2HPO_4$, 0.1 M/L NaCl and 2 mg./l of gentamicin sulfate. 212 milligrams, 265 milligrams and 318 milligrams of $Na_2CO_3$ was added to each aliquot, respectively, thus providing three aliquots with $Na_2CO_3$ levels of 20 millimole/liter, 25 millimole/liter and 30 millimole/liter, respectively. When all the $Na_2CO_3$ is dissolved, each diluent aliquot was added to a respective hemoglobin aliquot of 55.6 milliliters with stirring. Ten milliliters of the diluted hemoglobin solution from each aliquot was tonometered at 25° C. with 7.5 percent $O_2$ and 3.5 percent $CO_2$ for 20 minutes. The tonometered solutions were tested on a blood gas analyzer. The pH of each solution was tested. The pH of one of the solutions was above the desired pH (which, in this case, is 7.400) and another was below that value. A linear relationship between pH and millimolarity of the $Na_2CO_3$ was assumed and an aliquot was prepared based on that assumption. The new aliquot was tonometered and analyzed. This procedure was repeated until the aliquot had the desired pH (in this case, 7.400±0.010). The amount of $Na_2CO_3$ as determined above was added to the bulk diluent. In this example the pH of the final adjusted aliquot was 7.402 when 27 millimoles of $Na_2CO_3$ was added to an aliquot of the hemoglobin. The volume of the hemoglobin to be diluted was 30 liters and, therefore, 24 liters of the diluent containing 27 millimoles/liter of $Na_2CO_3$ was added for a final volume of 54 liters. Thus, 154.5 grams of $Na_2CO_3$ was added to the diluent prior to the addition of the stroma-free hemoglobin solution. The diluent as prepared above was added slowly to the hemoglobin solution with stirring. The diluted hemoglobin solution was transferred to a suitable sterile container through a Pall NR filter. A small sample was removed from the bulk hemoglobin solution and tested to determine that no bacterial growth occurred. The sterile, diluted hemoglobin solution was equilibrated with the desired amount of gas in order to obtain the desired level of pH, $P_{O2}$ and $P_{CO2}$. This equilibration was achieved in this specific example by prewarming the hemoglobin solution by passing it through a stainless steel coil in a 25° C.±0.2° C. water bath. The solution was passed through a series of C-DAK-2.5D artificial kidneys and into a sterile bottle containing a coil connected to a circulator bath to maintain it at 25° C.±0.2° C. A countercurrent of gas which had been prewarmed to 25° C.±0.2° C. by passage through a coil and humidified to saturation by bubbling through water at 25° C. was passed through the outside of the kidneys. The gas was then fed into the equilibration bottle to maintain an atmosphere over the solution of the same gas with which the solution was equilibrated. After all the hemoglobin solution was removed from its original container, connections were made to provide for recycling of the solution through the 25° C. coil and kidneys with return to the equilibrium container. Samples were removed from the solution during equilibration and tested on blood gas analyzers.

The equilibrated solution showed stable values for pH, $P_{O2}$ and $P_{CO2}$ at the target level for one hour prior to final sterile filtration.

The final bulk container, connected to the filter apparatus, was purged well with the gas having 7.5 percent $O_2$ and 3.5 percent $CO_2$. A coil inside the container was connected to a circulator to maintain the temperature of the filtered bulk at 25° C.±0.2° C. The equilibrated bulk was pumped through the sterile filter apparatus. A slight positive gas pressure was maintained on the bulk container during transport to the filling area.

The equilibrated hemoglobin solution was filled into two ml. ampules using a fill dose of 1.5 milliliters. The ampules were preflushed with the gas mixture used for equilibration and overfilled with the same gas after filling. Discontinuous flushing using a flow of 50 cubic feet per hour was used. Bulk temperature was maintained at 25° C. by means of a coil connected to a water circulator. A slight positive pressure of the humidified gas, used for equilibration, was maintained over the bulk container.

The ampules were sealed and ready to be opened when used as a blood gas reference fluid.

EXAMPLE 2

Example 1 was repeated except that the target pH was 7.10±0.010 with $P_{O2}$ levels and $P_{CO2}$ levels of 155 mm. Hg and 20 mm. Hg, respectively. In order to obtain the proper pH, aliquots containing $Na_2CO_3$ levels of 5 millimoles/liter, 7.5 millimoles/liter and 10 millimoles/liter were prepared and added to the aliquots of the hemoglobin solution. The tonometry results showed that 7.5 millimoles gave the desired pH. The procedure of Example 1 was followed. The final blood gas control fluid had $O_2$ and $CO_2$ levels of 154 mm. Hg and 19 mm. Hg, respectively, and a pH of 7.10.

EXAMPLE 3

Example 1 was repeated except that the target pH was 7.60±0.01 with the desired $O_2$ and $CO_2$ levels being 55 mm. Hg and 70 mm. Hg, respectively. The level of $Na_2CO_3$ in the three aliquots were 40 millimoles/liter, 50 millimoles/liter and 60 millimoles/liter. Following the procedure of Example 1, 47 millimoles were determined to give the desired pH. The process was completed as in Example 1. The final pH of the blood gas control fluid was 7.60 and had an $O_2$ level and a $CO_2$ level of 54 mm. Hg and 69 mm. Hg, respectively.

Thus, in accordance with the present invention, a blood gas reference fluid is provided which is relatively stable and accurately reflects levels of blood gas constituents and pH comparable to blood samples to be analyzed. Further, in accordance with the present invention, a blood gas control fluid is provided which can be prepared at various levels of pH, $P_{O2}$ and $P_{CO2}$ for standardization of blood gas instrumentation.

Although the invention has been described with reference to specific materials and specific methods, the invention is only to be limited so far as set forth in the accompanying claims.

We claim:

1. A stable reference fluid comprising substantially pure stroma-free hemoglobin solution, a source of bicarbonate ion, a buffer and predetermined amounts of gases present in in vivo blood.

2. The reference fluid of claim 1 in which the source of bicarbonate ion is sodium carbonate.

3. The reference fluid of claim 2 wherein said sodium carbonate is present at a level of up to 75 millimoles/liter of solution.

4. The reference fluid of claim 1 containing oxygen.

5. The reference fluid of claim 4 wherein the partial pressure of oxygen ($P_{O2}$) is between 10 and 500 mm. Hg at 37° C.

6. The reference fluid of claim 1 containing $CO_2$.

7. The reference fluid of claim 6 wherein the partial pressure of carbon dioxide ($P_{CO2}$) is between 5 and 100 mm. Hg at 37° C.

8. The reference fluid of claim 1 containing an electrolyte.

9. The reference fluid of claim 1 having a pH of 6.8 to 8.0.

10. The reference fluid of claim 1 packaged in a sealed ampule impermeable to air.

11. A stable reference fluid for use in calibration and control of blood gas instruments which comprises substantially pure stroma-free hemoglobin, a source of bicarbonate ion, a buffer, and electrolyte, and predetermined amounts of oxygen and carbon dioxide.

12. A stable reference fluid for use in calibration and control of blood gas instruments which comprises a substantially pure stroma-free hemoglobin solution containing 6 to 18 percent hemoglobin, up to 75 millimoles/liter of solution of sodium carbonate, a buffer, an electrolyte, oxygen in an amount sufficient to provide a partial pressure of 10 to 500 mm. Hg at 37° C., and carbon dioxide in an amount sufficient to provide a partial pressure of 5 to 100 mm. Hg at 37° C., the pH of the fluid being between 6.8 and 8.0.

* * * * *